US007008646B2

(12) United States Patent
Spicer et al.

(10) Patent No.: US 7,008,646 B2
(45) Date of Patent: *Mar. 7, 2006

(54) CUBIC LIQUID CRYSTALLINE COMPOSITIONS AND METHODS FOR THEIR PREPARATION

(76) Inventors: Patrick Thomas Spicer, 442 Hillcrest Dr., Wyoming, OH (US) 45215; William Broderick Small, II, 7281 Krach Ct., Liberty Township, OH (US) 45044; Matthew Lawrence Lynch, 3769 Harvard Acres, Mariemont, OH (US) 45227

( * ) Notice: Subject to any disclaimer, the term of this patent is extended or adjusted under 35 U.S.C. 154(b) by 380 days.

This patent is subject to a terminal disclaimer.

(21) Appl. No.: 09/990,552

(22) Filed: Nov. 21, 2001

(65) Prior Publication Data

US 2002/0160040 A1 Oct. 31, 2002

Related U.S. Application Data

(60) Provisional application No. 60/269,953, filed on Feb. 20, 2001.

(51) Int. Cl.
*A61K 9/14* (2006.01)

(52) U.S. Cl. .................. 424/490; 424/489; 424/493; 424/494

(58) Field of Classification Search ................ 424/489, 424/490, 493, 494, 451
See application file for complete search history.

(56) References Cited

U.S. PATENT DOCUMENTS

| 5,531,925 | A | | 7/1996 | Landh et al. |
|---|---|---|---|---|
| 5,756,108 | A | * | 5/1998 | Ribier et al. ................. 424/401 |
| 5,811,406 | A | | 9/1998 | Szoka, Jr. et al. |
| 5,972,373 | A | | 10/1999 | Yajima et al. |
| 6,017,388 | A | * | 1/2000 | Yuan ...................... 106/210.1 |
| 6,299,798 | B1 | | 10/2001 | Guerin et al. |
| 6,656,385 | B1 | * | 12/2003 | Lynch et al. ............ 252/299.61 |
| 2002/0153509 | A1 | * | 10/2002 | Lynch et al. ............ 252/299.01 |

FOREIGN PATENT DOCUMENTS

| WO | WO 96/03056 A1 | 2/1996 |
|---|---|---|
| WO | WO 99/12640 A1 | 3/1999 |
| WO | WO 99/47004 A1 | 9/1999 |
| WO | WO 00/23517 A1 | 4/2000 |
| WO | WO 01/68139 A1 | 9/2001 |

OTHER PUBLICATIONS

Gustafsson, J. et al., "Submicron Particles of Reversed Lipid Phases in Water Stabilized by a Nonionic Amphiphilic Polymer", LANGMUIR, 13, pp. 6964-6971 (1997).

Hyde, S. et al., "Cubic Phases", The Language Of Shape, Chapter 5, pp. 203-208 (1997).

(Continued)

*Primary Examiner*—James M. Spear
(74) *Attorney, Agent, or Firm*—Frost Brown Todd, LLC

(57) ABSTRACT

A dry powder cubic gel precursor comprising an encapsulating compound, an amphiphile capable of forming a cubic liquid crystalline phase, and optionally a solvent. The encapsulating compound (A), amphiphile (B), and optional solvent (C) are present in mass fractions relative to each other such that 1.0=a+b+c wherein a is the mass fraction of A, b is the mass fraction of B, and c is the mass fraction of C. Further, 1.0>a>0, 1.0>b>0, 1.0>c>0 and a, b, and c do not fall within a cubic liquid crystalline phase region on a phase diagram representing phase behavior of A, B, and C.

16 Claims, 6 Drawing Sheets

OTHER PUBLICATIONS

Laughlin, R. G., "An Expedient Technique for Determining Solubility Phase Boundaries in Surfactant-Water Systems", Journal Of Colloid And Interface Science, vol. 55, No. 1, pp. 239-242 (1976).

Hecht, E., "Birefringence", OPTICS, 3$^{rd}$ Edition, pp. 330-342 (1998).

Rosevear Ph.D., F. B., "Liquid Crystals: The Mesomorphic Phases of Surfactant Compositions", Journal Of Society Of Cosmetic Chemists, 19, pp. 581-594 (1968).

Laughlin, R. G., Surfactant and Nonsurfactant Behavior, The Aqueous Phase Behavior Of Surfactants, Chapter 9, p. 255 (1994).

Porter, M. R., "Nonionics", Handbook Of Surfactants, 2$^{nd}$ Edition, pp. 188-236.

Lynch, M. L., et al., "Aqueous-Phase Behavior and Cubic Phase-Containing Emulsions in the $C_{12}E_2$-Water System", LANGMUIR, 16, pp. 3537-3542 (2000).

Laughlin, R. G., "The Determination Of Phase Diagrams", The Aqueous Phase Behavior Of Surfactants, Appendix 4, pp. 521-546 (1994).

J. S. Kim, et al., *Drug Formulations that Form a Dispersed Cubic Phase when Mixed with Water*, Procced. Int'l. Symp. Control. Rel. Bioact. Mater., 27 (2000) Controlled Release Society, Inc., pp. 1118 & 1119.

* cited by examiner

CUBIC LIQUID CRYSTALLINE COMPOSITIONS AND METHODS FOR THEIR PREPARATION

CROSS REFERENCE TO A RELATED PATENT

This application claims priority to co-pending and commonly-owned, U.S. Provisional Application Ser. No. 60/269,953, titled, "Cubic Liquid Crystalline Compositions and Methods for Their Preparation"; filed Feb. 20, 2001, in the name of Patrick T. Spicer.

FIELD OF THE INVENTION

This invention relates to the production of powders that form cubic liquid crystalline particles upon hydration.

BACKGROUND OF THE INVENTION

Materials that enable the targeted delivery via controlled release of active materials can be valuable. Ideally, a delivery mechanism possesses high solubility for the active, robust containment abilities to avoid leakage during processing, storage and use, and is inexpensive and flexible for use with various active materials and delivery methods. Currently, vesicles or liposomes (dispersed lamellar liquid crystalline particles) can be used to contain and deliver active materials. However, liposomes are not long lasting, stable structures.

Liposome delivery alternatives include three forms of cubic liquid crystalline phase materials (precursor, bulk, and particulate (i.e. cubosomes)). Precursor materials are usually liquid and form a cubic phase in response to dilution. Bulk and particulate forms of cubic phase are viscous isotropic gel-like materials, often with an active ingredient, such as a drug, incorporated in its structure. Landh, U.S. Pat. No. 5,531,925 describes the production of powdered precursors by freeze-drying cubic phase particles containing proteins. However, the sticky nature of the monoglyceride and the high shear dispersion required to form cubic gel particles makes this type of powder difficult to work with as there is a tendency for clumping. Further, these types of powders are not necessarily colloidially stable upon hydration. Additionally, on a large scale, freeze-drying processes are significantly more expensive than spray-drying techniques. Finally, Landh does not discuss the encapsulation of a monoglyceride with encapsulants. It is believed that encapsulation can be necessary to form non-cohesive powders that form colloidally stable cubic liquid crystalline particles upon hydration.

Further, after complete hydration of the monoolein to form a bulk or particulate dispersion form of cubic phase, the cubic phase is then applied to a target environment, such as body tissue. The active can then diffuse out of the cubic phase in a controlled release fashion as a result of its complex internal bicontinuous structure. Cubic phase particles are typically produced by high-energy dispersion of bulk cubic gel, followed by colloidal stabilization through significant addition of polymer, up to 12% w/w according to Gustafsson et al., "Submicron particles of Reversed Lipid Phases in Water Stabilized by a Nonionic Amphiphilic Polymer," Langmuir, 13, 6964–71 (1997), herein incorporated by reference. This type of process can require a significant amount of water and energy input thereby limiting the flexibility of a formulation using such particles.

Leser, WO 99/47,004, discloses a food ingredient in aqueous or instant powder form, containing a monoglyceride that forms a cubic, lamellar or hexagonal structure encapsulating or associating the food ingredient. Leser is primarily concerned with the encapsulation of food ingredients with liquid crystalline materials. However, Leser does not disclose the use of a hydrotrope additive in powder formation to avoid the formation of cubic liquid crystalline gel during drying. Additionally, Leser does not disclose powder precursors that form cubic liquid crystalline particles that are immediately colloidally stabilized upon hydration.

Yuan, WO 00/23,517, discloses a high-amylose starch-emulsifier (monoglyceride) composition forming a complex for food and beverage applications. This complex is used to incorporate fat into food formulations rather than create liquid crystalline particles. Powder, gel, and paste forms are disclosed for food property adjustment, not controlled-release or pharmaceutical applications. Yuan does not disclose the use of hydrotrope to avoid liquid crystalline formation during drying of powders.

Nickel, WO 96/03,056, describes inclusion complex production for use as delivery vehicles of fats and oils into food products as emulsions. Again, Nickel does not disclose controlled-release liquid crystalline particles or the use of hydrotropes.

Szoka, U.S. Pat. No. 5,811,406, discloses freeze-dried powders forming "lipoplexes" or lamellar liquid crystalline liposomes complexed with DNA and other biological proteins. The powders can be used to deliver the bioactive materials to the respiratory tract, where they hydrate to form lamellar liposomes that deliver the bioactives to the adjacent cells. While monoolein is specified as a surfactant for use in forming liposomes, it is only in combination with other surfactants and is not used to form cubic phase. Cubic liquid crystalline particles are more robust (against degradation) than and structurally distinct from liposomes.

Guerin, WO 97/15,386, discloses the formation of detergent granules containing liquid-phase active ingredients by spray-drying a water-in-oil emulsion that lacks a cubic phase. Hydration of these powders does not produce colloidally stable particles but instead forms a detergent solution. Additionally, Guerin does not disclose additional starting liquids like isotropic solutions and liquid crystalline materials, nor do they utilize encapsulating compounds.

Anderson, WO 99/12,640, discloses bicontinuous cubic liquid crystalline particles coated by solid crystalline materials (i.e., metals) as controlled delivery and uptake devices that either shed their coating to function or have a porous coating. These particles, however, are limited to having nanostructured liquid or liquid crystalline materials (such as a fully hydrated bicontinuous cubic phase) in their cores. Further, the use of encapsulants that dissolve and provide colloidal stabilizaion benefits or the use of hydrotropes to aid a spray-drying processes are not mentioned.

Finally, Yajima et al., WO 96/34,628, discloses a drug having an unpleasant taste, a polymer solution in the stomach, and monoglyceride crystals. There is no use of the unsaturated monoglyceride, monoolein, only the saturated monostearin. Additionally, bicontinuous cubic or cubic hybrid liquid crystalline structures are not disclosed.

As used herein, "Amphiphilic substance" means a molecule with both hydrophilic and hydrophobic (lipophilic) groups. Amphiphilic substances generally spontaneously self-associate in aqueous systems and form various aggregates. Exemplary, but non-limiting, aggregates include lamellar phases, hexagonal phases, and cubic phases. These phases are thermodynamically stable. The long-range order in these phases, in combination with liquid-like properties in the short-range order, gave rise to the notation "liquid crystalline phases".

Cubic Gel Precursors

Smectic liquid crystalline phases (i.e., bulk cubic liquid crystalline gels and dispersions of cubic liquid crystalline gel particles) can be formed from precursors including an amphiphilic molecule such as a lipid and a polar liquid. The cubic liquid crystalline gel phase structures can form in response to some event, such as a temperature change or dilution of the precursor. In some applications, a cubic gel precursor forms a bulk cubic liquid crystalline gel only when needed for the specific application. For example, precursors have been used in antiperspirants, in which a water-insoluble liquid crystalline phase forms when the precursor contacts sweat (salt water). The resulting bulk liquid crystalline gel has a cubic or hexagonal liquid crystal structure that blocks pores. Precursors have also been used to deliver a therapeutic agent to treat periodontal disease, for example, by putting the precursor comprising a monoglyceride and an active ingredient into a reservoir such as a periodontal pocket. The precursor forms bulk cubic liquid crystalline gel on contact with saliva and then provides controlled release of the therapeutic agent.

However, in these applications, some uncontrolled stimulus (such as sweating or salivating) is required for the precursor to form a bulk cubic liquid crystalline gel. Further, the precursor is generally not a powder, but a liquid. Control of the bulk cubic liquid crystalline gel properties can be difficult. Furthermore, it can be difficult to form a particulate cubic liquid crystalline gel directly from the precursor. Therefore, there is a need to provide a substantially dehydrated precursor that can directly form either bulk or particulate cubic liquid crystalline gels. There is a further need to provide a method for using the precursor to prepare bulk and particulate cubic liquid crystalline gels with controlled properties.

Bulk Cubic Liquid Crystalline Gel

The liquid crystalline phases have distinct hydrophilic and hydrophobic domains, which give them the ability to dissolve (solubilize) or disperse water-soluble, oil-soluble, and amphiphilic compounds. Liquid crystalline phases are highly ordered structures that restrict the diffusion of added ingredients, thereby making them useful for controlled-release purposes. Cubic liquid crystalline phases can be prepared as pastes and thus are particularly useful as delivery vehicles due to their rheological properties. Cubic liquid crystalline phases are also advantageous in that they are mechanically robust and resistant to physical degradation.

Bulk cubic liquid crystalline gels prepared in advance (i.e., before administration rather than in situ) can also be used as controlled release reservoirs of pharmaceutical materials. However, bulk cubic liquid crystalline gels can be difficult to prepare due to the properties of the raw materials and Theological properties of the gels themselves. Lipids that yield cubic liquid crystalline phases, such as monoglycerides, are typically waxy solids at room temperature. Therefore, the bulk cubic liquid crystalline gel is prepared by equilibration, at high temperature or over many hours, or both, because transport of water can be slow through solid lipids. Processes requiring long hold times at high temperatures to manufacture bulk cubic liquid crystalline gels are not economically, or commercially, practical. Therefore, a further need exists to provide a commercially feasible method for forming a bulk cubic liquid crystalline gel at relatively low temperature (e.g., room temperature), and in a relatively short amount of time (e.g., within minutes).

Bulk cubic liquid crystalline phases are high-viscosity, solid-like gels, which can make large-scale dispersed cubic liquid crystalline phase particles difficult because of the problems associated with mixing and homogenizing. High-energy input is required, potentially degrading liquid crystalline structures. For example, high-energy input processes such as those employing high shear can physically degrade crystalline structures. High-energy input processes, such as those employing high temperatures, can chemically degrade the compounds making up the liquid crystalline structures. Furthermore, high energy input processes are costly and require more precise control and maintenance. Therefore, there is a need to provide methods for preparing cubic liquid crystalline phase materials that are less costly and more efficient than the methods involving bulk solid processing.

Dispersed Cubic Liquid Crystalline Gel Particles

Lamellar phases have a bilayer sheet structure. When a lamellar phase is dispersed in excess water, the lamellar phase may form vesicles and liposomes. "Vesicle" means an enclosed shell comprised of one bilayer of amphiphilic molecules. "Liposome" means an enclosed shell comprised of more than one bilayer of amphiphilic molecules. Vesicles and liposomes can be spheroidal, ellipsoidal, or irregularly shaped; however, spheroidal shells are the most stable.

Vesicles and liposomes suffer from the drawback that they are non-equilibrium states, which means that, inevitably, they will degrade. Furthermore, vesicles and liposomes are relatively expensive to manufacture and are more fragile than cubic liquid crystalline particles to shear-induced destruction. Therefore, there is a need to provide a stable, less expensive alternative to vesicles and liposomes.

Bulk cubic liquid crystalline gel can also be dispersed to form particles. Dispersed particles of cubic liquid crystalline phases are structurally distinct from vesicles and liposomes. Dispersed cubic gel particles have a cubic or spherical outer structure with a bicontinuous cubic internal structure. The bicontinuous cubic internal structure has distinct hydrophilic and lipophilic domains, and is described in S. Hyde et al., *The Language of Shape*, Elsevier, Amsterdam, 1997, pages 205–208, herein incorporated by reference.

Typically, cubic liquid crystalline gel particles are formed via fragmentation and dispersion of homogeneous bulk cubic liquid crystalline gel in excess solvent (i.e. water). Fragmentation is typically carried out in the liquid phase in combination with stabilizer/fragmentation agents such as polysaccharides, proteins, amphiphilic macromolecules and lipids, amphiphilic polymers, and amphiphilic compounds. Fragmentation also requires the use of a high-energy input process by, for example, high shear milling or sonication.

Fragmenting and dispersing solid and solid-like materials, such as bulk cubic liquid crystalline gel, is difficult and impractical above very small processing scales (e.g., on the order of several grams, or less) without significant energy input and hold time. This makes commercial scale production of dispersed cubic gels expensive and impractical. Furthermore, high energy input processes can create non-equilibrium structures, such as vesicles and liposomes. Therefore, there is a need to develop a means for producing dispersed cubic liquid crystalline gel particles that does not require a fragmentation step. There is still a further need to provide a method for forming cubic gel particles instantaneously by hydrating dry powder precursors with solvent. There is currently no way to form cubic liquid crystalline particles from a dry powder precursor, all current fragmentation and precursor processes utilize relatively large fractions of liquid.

It is a further object of this invention to provide an economical and practical method for producing easy-flowing dry powders that can be easily used to prepare commercial-scale quantities of colloidally stabilized cubic liquid crystalline gel particle dispersions upon contact with water.

SUMMARY OF THE INVENTION

In a non-limiting exemplary embodiment of the present invention, a cubic gel precursor comprises an encapsulating compound, an amphiphile capable of forming a cubic liquid crystalline phase, and optionally a solvent. The encapsulating compound (A), amphiphile (B), and optional solvent (C) are present in mass fractions relative to each other such that $1.0 = a+b+c$ wherein a is the mass fraction of A, b is the mass fraction of B, and c is the mass fraction of C. Further, $1.0 > a > 0$, $1.0 > b > 0$, $1.0 > c > 0$. Additionally, a, b, and c do not fall within a cubic liquid crystalline phase region on a phase diagram representing phase behavior of A, B, and C.

Another non-limiting exemplary embodiment of the present invention includes the method of making a cubic gel precursor. First, an encapsulating compound is dissolved in a solvent and an amphiphile is added. Next, the encapsulating compound and the amphiphile are mixed. This method provides that these steps may be performed in any order. Third, the mixture is atomized. Finally, the resulting mixture is dried.

DETAILED DESCRIPTION OF THE INVENTION

Figure 1:
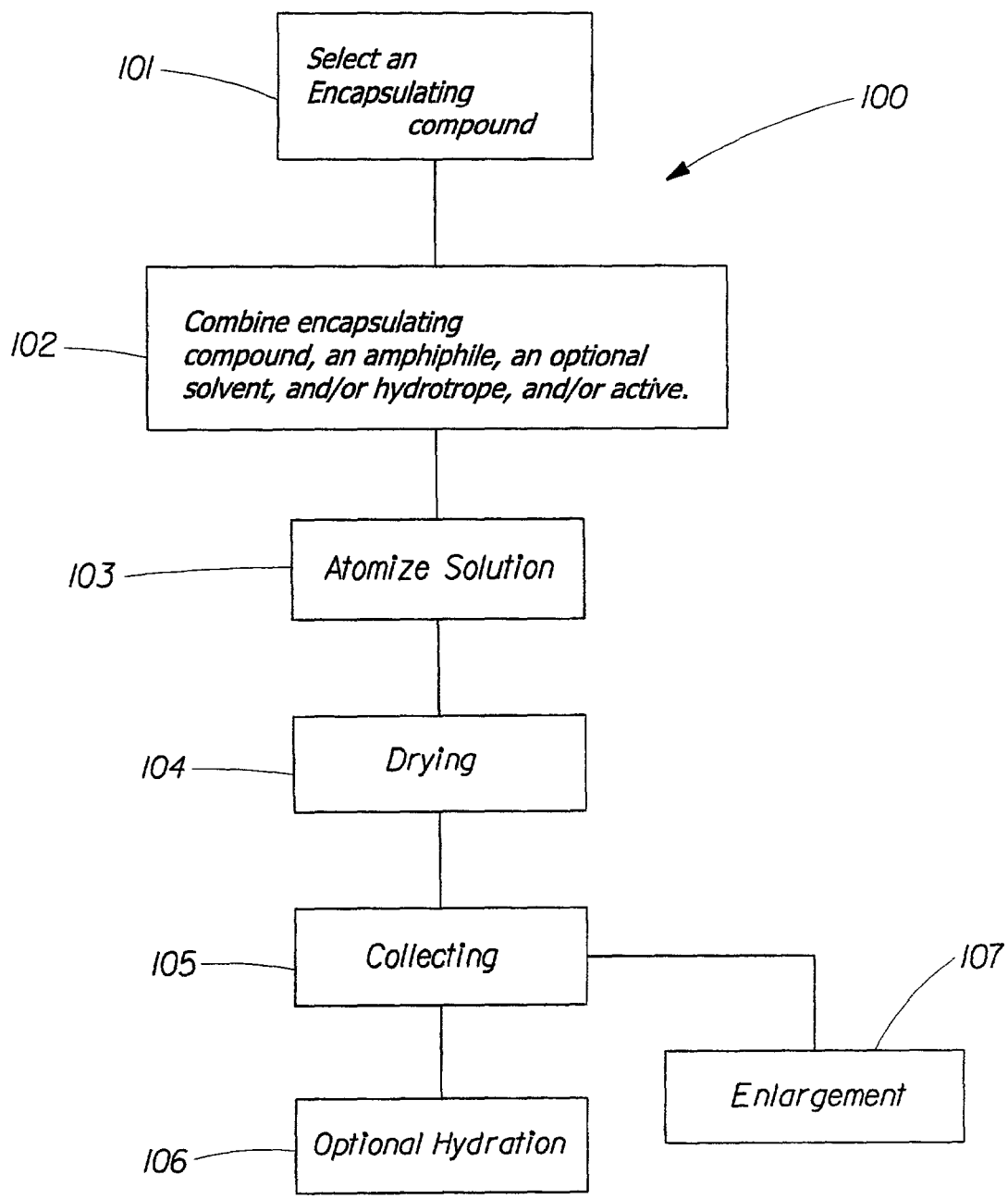
FIG. 1 is a flow diagram of the method steps for the preferred methods for preparing the powdered cubic gel precursor according to this invention.

Publications and patents are referred to throughout this disclosure. All U.S. Patents cited herein are hereby incorporated by reference. All percentages, ratios, and proportions used herein are by weight unless otherwise specified. All measurements are made at 25° C., unless otherwise specified.

It has been surprisingly found that flowable dry powders of encapsulated monoglycerides, upon addition to a solvent, can spontaneously hydrate to form a colloidally stable dispersion of cubic liquid crystalline and/or L3 liquid crystalline and/or hybrid cubic/lamellar and/or cubic/L3/lamellar liquid crystalline particles that release active materials via diffusion or triggered release. Further, in large-scale processes, it is often more desirable to work with dry powder or granular materials rather than with more dilute liquid phase products. Powders avoid the need for transport of bulk water, an expensive and inefficient prospect, by providing a more concentrated active material form. In addition, a wider range of applications (for example, inhalation delivery of drugs and vaccines) is available for cubic phase when a dry powder precursor is considered.

Definition and Usage of Terms

The following is a list of definitions for terms, as used herein:

"Amphiphile" means a molecule with both hydrophilic and hydrophobic (lipophilic) groups (e.g, surfactants, lipids, and polymers).

"Bulk cubic gel" means a viscous, structurally isotropic gel (clear, translucent, or opaque) having a normal or reversed cubic liquid crystalline structure, with a composition matching a cubic liquid crystalline region of a phase diagram representing the phase behavior of a hydrotrope, a surfactant, and a solvent.

"Encapsulating compound" means a material that at least partially forms an encapsulating shell or matrix around an amphiphile or an amphiphile and active.

"Colloidally stable" means cubic gel particles dispersed in a solvent so that the particles do not coalesce, flocculate, or agglomerate over time.

"Cubic gel precursor" means a formulation that will form a cubic liquid crystalline phase upon action by a stimulus. The stimulus can be the addition of some specified material such as additional hydrotrope, amphiphile, or solvent; the removal of some specified material such as a portion of the hydrotrope, amphiphile, or solvent; application of an external field (including, but not limited to, fluid shear and electrical fields), a temperature change; a pressure change; addition of salt; or a pH change in aqueous systems.

"Cubic gel particles" means the dispersed form of bulk cubic gel; technically they are cubic liquid crystalline gel in equilibrium or in a metastable state with the solvent, isotropic liquid phase, L3 phase, lamellar phase, or a combination of two of these.

"Gel" means a Theologically semisolid system. Gel includes cubic liquid crystalline materials such as bulk cubic gels and dispersions of cubic gel particles.

"Hydrotrope" means a surfactant-type molecule (comprising at least one hydrophilic group and at least one hydrophobic group), wherein the molecule has too short or too soluble a hydrophobic group or too insoluble or too large a hydrophilic group to display surfactant phase behavior. Hydrotropes are highly soluble in water and do not form aggregates in solution (e.g., micelles). Hydrotropes dissolve amphiphiles. Hydrotropes do not prevent formation of a cubic liquid crystalline phase upon dilution of a mixture of the hydrotrope and amphiphile with a solvent. The hydrotropes enhance the miscibility of weakly polar and otherwise water-insoluble molecules (such as monoolein) with aqueous solutions; this effect is commonly known as "salting-in". The hydrotrope is typically present in a substantial concentration (i.e., 1% or more) to display the hydrotropic properties described above. The hydrotrope may be solid or liquid at room temperature and may be water-soluble or water-insoluble.

"L1" means a dilute liquid phase.

"L2" means a concentrated liquid phase.

"L3" means a disordered bicontinuous liquid crystalline phase (often termed "sponge").

"Lipid" means any amphiphilic molecule of intermediate molecular weight that contains a substantial portion of aliphatic or aromatic hydrocarbon.

"Paste" means a liquid for topical application, preferably to the skin of an animal (preferably a human), whose viscosity is enhanced to the point that flow is largely inhibited by the presence of undissolved, as well as dissolved, solids.

"Stabilizer" means an agent that prevents aggregation, coalescence, and flocculation of dispersed phase particles. Stabilizers impart colloidal stability to dispersed cubic gel particles. Stabilizers include polymers, small particulates that absorb upon surfaces of the particles, ionic materials, and liquid crystalline phase adsorbed to the surfaces of the particles.

"Surfactant" means an amphiphile that exhibits the following properties in water: (1) it reduces the interfacial tension, and (2) it self-assembles in solution at low concentrations.

"Thermodynamically stable" means a system in the lowest possible energy state.

Compositions

This invention relates to cubic gel precursors, bulk cubic gels, and cubic gel particles and methods of producing the same.

Cubic Gel Dry Powder Precursor

The cubic gel dry powder precursor comprises (A) an encapsulating compound, (B) an amphiphile, and optionally (C), a solvent. The precursor may optionally further comprise (D) a hydrotrope, and/or (E) an active ingredient. It is preferred that the precursor does not form a cubic phase gel until hydration of the powder occurs. It is also an alternative embodiment that the active ingredient (E) also serve as a hydrotrope and an active ingredient thereby combining components (D) and (E).

Encapsulating Compound

Ingredient (A) is an encapsulating compound. Encapsulated powders have a structure distinct from freeze-dried monoglycerides and when hydrated form cubic liquid crystalline particles. Generally, any polysaccharide polymer will act as an encapsulant when dehydrated by drying. Hydrophobically modified starches are exemplary, but non-limiting, encapsulating compounds because of their good shell-forming and emulsifier properties. Exemplary, and non-liming encapsulating compounds include wheat starch that is about 21–29% amylose, and potato starch, which is around 24% amylose. Materials such as cyclodextrin, dextran, and combinations thereof can also provide satisfactory encapsulating compounds. Additional exemplary and non-limiting encapsulating compounds include polysaccharide polymers, positively charged surfactants, negatively charged surfactants, hydrophobically modified polymers, mannose, lactose, casein, and Polxamer 407 and combinations thereof.

Hydrotrope

Ingredient (D) is a hydrotrope. The hydrotrope is preferably capable of dissolving the amphiphile. It is preferred that the hydrotrope not prevent formation of a cubic liquid crystalline phase upon sufficient dispersion of the cubic gel precursor in the solvent. Preferred hydrotropes allow for formation of cubic gel particles dispersed in isotropic liquid phases.

Suitable, but non-limiting, hydrotropes include low molecular weight alcohols; polyols; alcohol ethoxylates; surfactants derived from mono- and poly-saccharides; copolymers of ethylene oxide and propylene oxide; fatty acid ethoxylates; sorbitan derivatives; sodium butyrate; Poloxamer 407; Polyethylene glycol 400; dimethyl sulfoxide; sodium toluene sulfonate; nicotinamide; procaine hydrogen chloride; and ethylene glycol, propylene glycol, glycerol, and polyglyceryl esters, caffeine, sodium butyrate, nicotinamide, procaine hydrogen chloride, and the ethoxylated derivatives thereof, ethylene glycol, sodium alkanoates, sodium alkane sulfonates, Resorcinol, Pyrogallol, PABA hydrogen chloride, sodium p-bromobenzene sulfonate, isonicotinic acid, sodium 4-picolinate, sodium 3-hydroxy-2-napthlate, Sodium xylene sulfonate, sodium cinnamate, sodium benzene disulfonate, sodium p-toluene-sulfonate, sodium salicylate, sodium benzene sulfonate, sodium benzoate, sodium cumeme sulfonate, propylene glycol, glycerol, and polyglyceryl esters, caffeine, sodium butyrate; and combinations thereof and otherwise known to one skilled in the art of cubic gel precursor formulation.

More preferred hydrotropes include methanol, ethanol, 1,4,-butanediol, and combinations thereof. Without wishing to be bound by theory, it is believed that the hydrotrope should have sufficient hydrophilic character for cubic liquid crystalline phase to form when the hydrotrope is present in amounts up to about 10%.

One skilled in the art can determine whether a compound is suitable for use as a hydrotrope by preparing a composition comprising the compound to be tested for use as the hydrotrope, the selected amphiphile, and the selected solvent and allowing the composition to equilibrate, for example, by the method described below in Example 1. If the composition forms a cubic phase or cubic phase in combination with another phase, then the hydrotrope is suitable to use in this invention. If the composition forms a cubic phase or cubic phase in combination with an isotropic liquid, then the hydrotrope is preferred.

Polarized light microscopy (PLM) can be used to determine whether the composition formed a cubic phase. PLM can be carried out on a polarized light microscope or constructed light box, as described by Laughlin, R. G., *J. Colloid Interface Sci.*, 55, 239–242 (1976), herein incorporated by reference. Polarized light microscope textures define the phase/colloidal state of sample. Lamellar and hexagonal phases give birefringence (see Hecht, E., *Optics*, $3^d$ ed., Addison-Wesley Publishing Co., Reading, Mass., pp. 330–342 (1998)) and distinct textures such as Maltese Crosses (see Rosevear, F. B., *J. Am. Oil Chemists Soc.*, 19, 581–594 (1968)), both incorporated herein by reference. This is a consequence of the anisotropic phase structure of these particular phases, and their orientation relative to polarization of the light. However, L1, L2, L3, and cubic phases show no birefringence and appear dark in the microscope. Birefringence is a function of sample thickness, so sometimes it is difficult to see with a light microscope. Instead, the bulk sample can be placed in the aforementioned light box to secure a very thick sample.

Cubic phases are very viscous while the other phases (i.e., L1, L2, and L3) are less viscous, like water. Therefore, lack of birefringence in combination with bulk solid-like rheological properties indicates the presence of cubic phase.

Amphiphile Capable of Forming Cubic Liquid Crystalline Phase

Ingredient (B) is preferably an amphiphile that is capable of forming a cubic liquid crystalline phase. Ingredient (B) can be a single amphiphile or a combination (e.g., mixture) of two or more amphiphiles. Suitable amphiphiles are surfactants that should be capable of forming cubic liquid crystalline phases in the presence of ingredients (A) and (C) a solvent. Amphiphiles comprise a hydrophilic group and a lipophilic group. Suitable hydrophilic groups, and methods for the selection of suitable hydrophilic groups, are disclosed in Laughlin, R. G., *The Aqueous Phase Behavior of Surfactants*, Academic Press, New York, 1994, pp. 255, and International Patent Publication No. WO 99/12640, both incorporated by reference herein. An excerpt is presented in Tables 1–5 below:

TABLE 1

Anionic Hydrophilic Groups

| Functional Group | General Formula |
|---|---|
| Alkyl carboxylate salts | $RCO_2^-,M^+$ |
| Alkanesulfonate salts | $RSO_3^-,M^+$ |
| Alkyl sulfate salts | $ROSO_3^-,M^+$ |
| N-Alkylsulfamate salts | $RNHSO_3^-,M^+$ |
| Akylsulfinate salts | $RSO_2^-,M^+$ |
| S-Alkylthiosulfate salts | $RSSO_3^-,M^+$ |
| Phosphonate salts | $RPO_3^=,2M^+$ |
| Phosphate monoester salts | $ROPO_4^=,2M^+$ |
| Phosphinate salts | $R(R')PO_2^-,M^+$ |
| Nitroamide salts | $RN^-NO_2,M^+$ |
| Trisulfonylmethide salts | $RSO_2(CH_3SO_2)_2C^-,M^+$ |
| Xanthate salts | $RSCS_2^-,M^+$ |

TABLE 2

Cationic Hydrophilic Groups

| Functional Group | General Formula |
|---|---|
| Quaternary ammonium salts | $RN^+(CH_3)_3,X^-$ |
| Primary, secondary, and tertiary ammonium salts | $RN^+H_n(CH_3)_{3-n}, X^-$ |
| N-alkylpyridinium salts | $RNC_5H_5^+,X^-$ |
| Quaternary phosphonium salts | $RP^+(CH_3)_3, X^-$ |
| Ternary sulfonium salts | $RS^+(CH_3)_2, X^-$ |
| Ternary sulfoxonium salts | $RS^+(\rightarrow O)(CH_3)_2, X^-$ |
| Bis(phosphoranylidyl) ammonium salts | $[R(CH_3)_3P\rightarrow N \leftarrow P(CH_3)_3R]^+, X^-$ |

TABLE 3

Zwitterionic Hydrophilic Groups

| Functional Group | General Formula |
|---|---|
| Ammonioacetates | $R(CH_3)_2N^+CH_2CO_2^-$ |
| Ammonio hexanoates | $R(CH_3)_2N^+(CH_2)_5CO_2^-$ |
| Ammonio alkanesulfonates | $R(CH_3)_2N^+(CH_2)_3SO_3^-$ |
| Ammonioalkyl sulfates | $R(CH_3)_2N^+(CH_2)NOSO_3^-$ |
| Trimethylammonioethyl alkylphosphonates | $RPO_2^-OCH_2CH_2N^+(CH_3)_3$ |
| Trimethylammonioethylphosphate acylglyceryl esters | $RCO_2CH_2CH(OH)CH_2OPO_2^-O(CH_2)_2N^+(CH_3)_3$ |

TABLE 4

Dipolar Hydrophilic Groups

| Functional Group | General Formula |
|---|---|
| Aliphatic amine oxides | $R(CH_3)_2N\rightarrow O$ |
| Phosphine oxides | $R(CH_3)_2P\rightarrow O$ |
| Phosphonate esters | $R(CH_3O)_2P\rightarrow O$ |
| Phosphate esters | $RO(CH_3O)_2P\rightarrow O$ |
| Arsine oxides | $R(CH_3)_2As\rightarrow O$ |
| Sulfoxides | $R(CH_3)S\rightarrow O$ |
| Sulfoximines | $R(CH_3)S(\rightarrow O) \rightarrow NH$ |
| Sulfone diimines | $R(CH_3)S(\rightarrow NH)_2$ |
| Ammonioamidates | $RC(O)N^-\!\!-\!N\!+\!(CH_3)_3$ |
| Amides | $RC(O)N(CH_3)_2$ |

TABLE 5

Single Bond Hydrophilic Groups

| Functional Group | General Formula |
|---|---|
| Primary Amines | $RNH_2$ |

In Tables 1–5, R represents a hydrocarbon group, preferably an alkyl group. M represents a metal atom. The subscript n is 1, 2, or 3. X represents a halogen atom. The groups in Tables 1–5 are exemplary and not intended to limit the scope of this invention set forth in the claims. One skilled in the art would be able to select appropriate hydrophilic groups without undue experimentation.

Suitable, but non-limiting, lipophilic groups include monovalent hydrocarbon groups, substituted monovalent hydrocarbon groups, and siloxanes. Suitable monovalent hydrocarbon groups preferably have 6 to 22 carbon atoms, more preferably, 8 to 22 carbon atoms, and most preferably, 10 to 18 carbon atoms. Non-limiting substituted monovalent hydrocarbon groups include halogenated monovalent hydrocarbon groups, typically having 6 to 22 carbon atoms. The monovalent hydrocarbon groups and substituted monovalent hydrocarbon groups can be saturated or unsaturated, branched or unbranched. Preferred branched hydrocarbon groups typically have 8 to 22 carbon atoms. Preferred linear hydrocarbon groups have 8 to 18 carbon atoms.

Suitable lipophilic groups are disclosed in Anderson, WO 99/12640 at pages 12–13. One skilled in the art would be able to select appropriate lipophilic groups without undue experimentation.

Suitable amphiphiles for ingredient (B) also include those disclosed in U.S. Pat. No. 5,756,108. These include 3,7,11, 15-tetramethyl- 1,2,3-hexadecanetriol, (phytantriol), N-2-alkoxycarbonyl derivatives of N-methylglucamine, and unsaturated fatty acid monoglycerides.

Suitable amphiphiles for ingredient (B) should also include surfactants having HLB values of 2.1 to 4.6, see Porter, M. R., *Handbook of Surfactants*, 2$^{nd}$ ed., Blackie Academic & Professional, pp. 188–236.

A preferred class of surfactants for use as ingredient (B) comprises monoglycerides having the general formula:

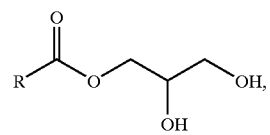

wherein R is selected from the group consisting of monovalent hydrocarbon groups of 6 to 22 carbon atoms, preferably 8 to 22 carbon atoms, more preferably 10 to 18 carbon atoms; and monovalent halogenated hydrocarbon groups of 6 to 22 carbon atoms. The monovalent hydrocarbon groups can be saturated or unsaturated, branched or unbranched. Preferred branched hydrocarbon groups typically have 8 to 22 carbon atoms. Preferred linear hydrocarbon groups have 8 to 18 carbon atoms. Preferred monoglycerides have a melting point $\geq 40°$ C. Anderson, WO 99/12640 discloses suitable amphiphiles that can form cubic liquid crystalline phase at pages 12–13 and 28–31.

Preferred, but non-limiting, amphiphiles for ingredient (B) include monoglyceride surfactants such as glycerol monooleate (HLB of 3.8), glycerol monostearate (HLB 3.4), ethoxylated alcohol surfactants such as $C_{12}EO_2$, $C_{12}EO_{23}$, and $C_{16}EO_3$, wherein EO represent an ethylene oxide group, (see Lynch et al., "Aqueous Phase Behavior and Cubic Phase-Containing Emulsions in the C12E2-Water System," *Langmuir*, Vol. 16, No. 7, pp. 3537–3542 (2000), incorporated by reference herein), monolinolein, and combinations thereof.

As long as the monoglyceride has sufficient purity to form cubic liquid crystalline phase in combination with solvent and the hydrotrope, the monoglyceride is suitable for ingredient (B). The monoglyceride is typically greater than about 40% to 100% pure, preferably about 82.5 to 100% pure. However, monoglycerides having purity less than about 40% may also be suitable.

Some diglyceride and triglyceride impurities can prevent the monoglycerides from forming cubic liquid crystalline phases. Therefore, the monoglycerides are preferably free of amounts diglyceride and triglyceride impurities high enough to prevent the monoglycerides from forming cubic liquid crystalline phases.

Suitable monoglycerides are known and are commercially available. Preferred, but non-liming, monoglycerides include glycerol monooleate available under the tradename DIMODAN® from Danisco A/S doing business as Grindsted Products A/S of Denmark.

Solvent

Ingredient (C) is a solvent. Ingredient (C) can be polar or nonpolar. Suitable, but non-liming, polar solvents include water, glycerol, polyglycols such as polyethylene glycol, formamides such as formamide, n-methyl formamide and dimethylformamide, ethylammonium nitrate, and combinations thereof. Suitable, but non-limiting, nonpolar solvents include oily solvents such as hydrocarbons and substituted hydrocarbons (e.g., halogenated hydrocarbons). Hydrocarbons are exemplified by alkanes and fatty esters such as lanolin. It is preferred that the solvent not break down liquid crystals, therefore, some amphiphilic oils and fatty acid diglycerides can be unsuitable for use as the solvent.

The amounts of each ingredient in the precursor depend on the phase behavior of the specific ingredients selected. Cubic gel precursor comprises a composition wherein the amounts of ingredients (A), (B), (C), (D), and (E) match any area of the phase diagram not already comprising cubic phase (i.e., containing no cubic phase alone and no cubic phase in equilibrium with another phase). One skilled in the art would be able to select appropriate amounts of each ingredient without undue experimentation by using a phase diagram.

The dry powder precursor can be used in an application where formation of cubic liquid crystalline particles is desired under a certain set of conditions. The powders are formulated such that the presence of sweat, saliva, or other liquids will change the system composition such that it is in the area surrounding either of the two cubic phases or within the two cubic phases. As a result, the mass fractional composition of the system of components (A), (B), (C), (D), and (E) relative to each other needs to simply obey the following equation:

$$1.0 = a+b+c+d+e$$

wherein a is the mass fraction of ingredient (A), b is the mass fraction of ingredient (B), and c is the mass fraction of ingredient (C), d is the mass fraction of ingredient (D), e is the mass fraction of ingredient (E), and $1.0>a>0$, $1.0>b>0$, $1.0>c>0$, $1.0>d>0$, $1.0>e>0$. Preferably, a, b, c, d, and e are all greater than zero. More preferably, the mass fraction of ingredient (A), the mass fraction of ingredient (B), and the mass fraction of ingredient (C) satisfy the equation:

$$1.0 = a+b+c$$

wherein $1.0>a>0$, $1.0>b>0$, and $1.0>c>0$, and most preferably 0.75 a 0.5, 0.5 b 0.25, and 0.2 c 0. Further, a, b, and c preferably do not fall within a cubic liquid crystalline phase region on a phase diagram representing the phase behavior of A, B, and C.

Phase diagrams can be used for any system comprising ingredients (A), (B), and (C) to determine the amounts of each ingredient in the cubic gel precursor, bulk cubic gels, and cubic gel particle dispersions of this invention. Phase diagrams can be obtained by one skilled in the art without undue experimentation using, for example, the methods disclosed by Laughlin, R. G., *The Aqueous Phase Behavior of Surfactants*, Academic Press, Inc., 1994, pp. 521–546, incorporated by reference herein.

The dry powder cubic precursor of this invention may be used to directly form dispersed cubic liquid crystalline particles, simply by adding solvent to the powder to hydrate it.

Dispersed Cubic Liquid Crystalline Gel Particles

This invention further relates to powdered particles that, upon hydration, form cubic liquid crystalline gel particles, and dispersions thereof. The cubic liquid crystalline gel particles have the same composition as that described above for the bulk cubic gel, however, the form differs. The particles have a particulate form, rather than a bulk gel. The particles typically range in size from at least about 5 nanometers to at least about 1000 micrometers, more preferably, from at least about 5 nanometers to at least about 100 micrometers, most preferably, from at least about 50 nanometers to at least about 10 micrometers. The dispersion comprises (A), an encapsulating compound, (B), an amphiphile capable of forming a cubic liquid crystalline phase, (C), a solvent, optionally (D), a hydrotrope, and optionally (E) an active ingredient.

Methods of the Invention

This invention further relates to methods for preparing the cubic gel precursor, bulk cubic liquid crystalline gel, and dispersed cubic liquid crystalline gel particles described above.

Cubic Gel Precursor

A preferred method for the preparation of a cubic gel precursor of this invention comprises the steps of first, warming water to a temperature between 10° C. and 70° C., depending on the encapsulating compound (A) selected as would be known to one skilled in the art without undue experimentation. Next, the encapsulating compound is agitated into water. Third, the encapsulating compound is fully dissolved into this solution until no particles are visible to the naked eye. Fourth, a hydrotrope may be added and/or a monoolein/active solution. Next, the solution is agitated in relation to the hydrotrope level as would be known to one skilled in the art. Finally, the precursor solution is fed into drying apparatus liquid feed nozzle. However, as would be known to one of skill in the art, freeze-drying, spray drying, fluidization, and combinations thereof can accomplish the drying step.

Figure 6:
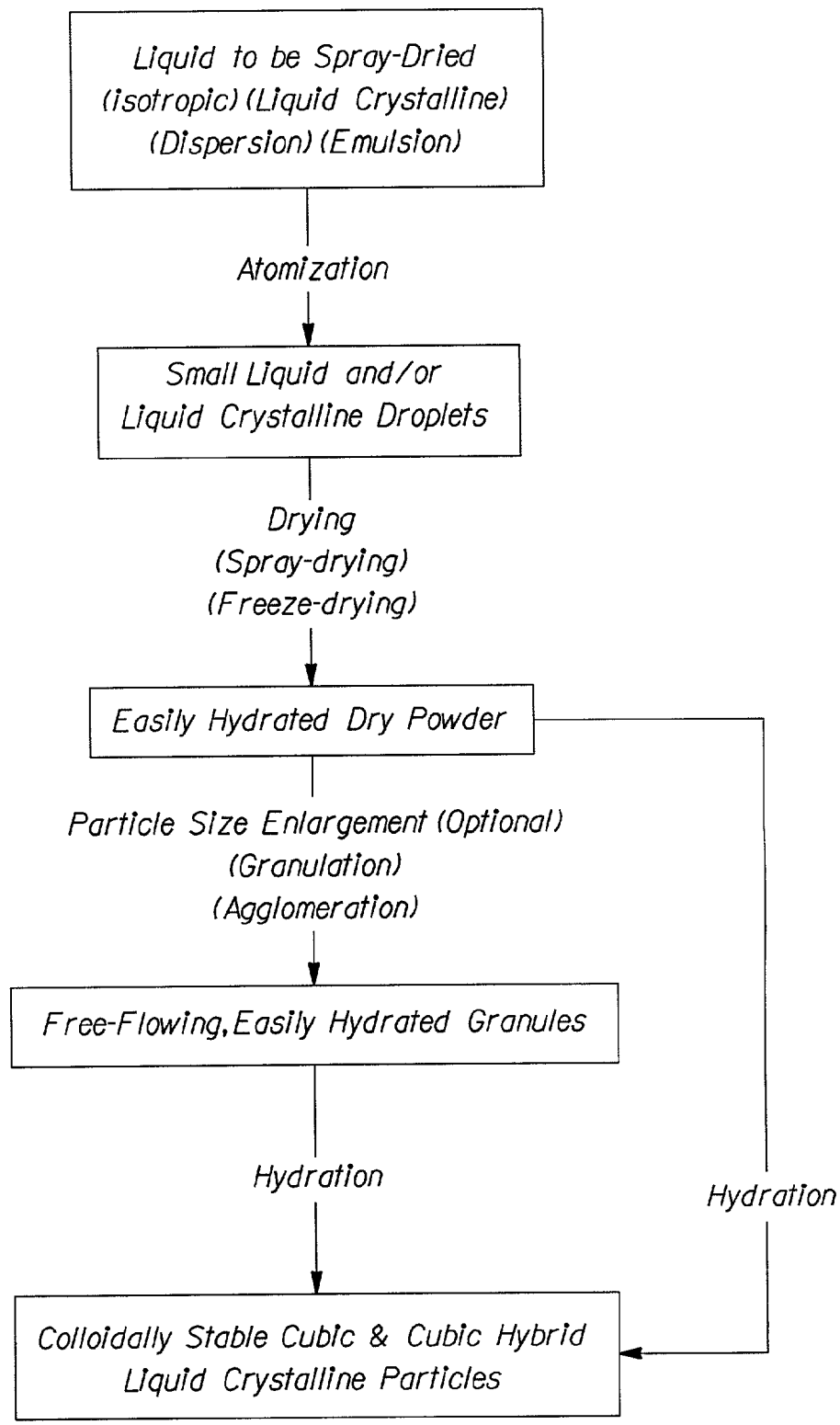
FIG. 6 is a flow diagram of the method steps for the preferred methods for increasing particle size.

As shown in FIG. 6, optionally, the powders produced above could have their flowability and dissolution kinetics enhanced by increasing the particle size by agglomeration or granulation to produce larger granules.

Dispersed Cubic Liquid Crystalline Gel Particles

Dispersed cubic liquid crystalline gel particles can be prepared from the powdered precursor particles described above. Additionally, a dispersion of cubic gel particles can be prepared directly from the powdered precursor by a method comprising a dispersing step of either dispersing the precursor in a solvent or, dispersing solvent in the precursor and thereafter diluting without a need for stabilization. It is believed that the product is stabilized (i.e., sterically stabilized) against flocculation by the presence of the encapsulating compound on its surface and interior.

FIG. 1 is a flow diagram 100 showing methods for preparing powdered particles that are precursors to cubic liquid crystalline particles and need only the addition of water to form. In each method, a liquid is prepared by selecting an encapsulating compound and then combining: (A) the encapsulating compound and (B) an amphiphile that is capable of forming cubic liquid crystalline phase structures and optionally (C), a solvent, and optionally (D), a hydrotrope, and optionally (E), an active ingredient to form any one of several forms including but not limited to an isotropic liquid, a liquid crystalline material, an emulsion, or a dispersion 102. Next, the above liquid is atomized 103 to produce small high surface area droplets. The droplets are then dried 104 by various techniques including co-current flow of hot, dry air. The free-flowing powders collected 105 may then be hydrated 106 to form cubic and/or cubic hybrid liquid crystalline particles or may be enlarged 107 to form granules that dissolve even more rapidly and flow even better than the above powders. After this, there are several viable preferred processes for preparing dispersions of cubic gel particles.

The particles formed in the dispersions typically have particle sizes in the range of about 50 nanometers to about 100 micrometers. However, the exact particle size range can depend on the method used.

Methods of Use

The precursors of this invention can be used as delivery vehicles or uptake vehicles. As a non-limiting example, a powder could be produced encapsulating a vitamin active ingredient. The encapsulation could protect the vitamin against oxidation and, with the addition of liquid, the powder forms cubic liquid crystalline particles that release the vitamin in a controlled or triggered fashion.

In a preferred, but non-limiting, embodiment of the invention, the precursors, bulk cubic gels, and particularly the dispersions and cubic gel particles of this invention are used as delivery vehicles in pharmaceutical and cosmetic compositions. The compositions may further comprise one or more pharmaceutically active ingredients, such as non-steroidal anti-inflammatory drugs (e.g., ketoprofen), or cosmetic ingredients, such as perfumes or dyes. In a more preferred embodiment of the invention, the active ingredient also has hydrotropic properties and may be used in addition to the hydrotrope described above as component (D). Alternatively, the active ingredient may be used instead of component (D), or instead of a portion of component (D). Compositions containing an active ingredient can be prepared by the methods described above, wherein the active ingredient is added concurrently with component (D).

Further still, the active ingredient can be selected from known proteins, amino acids, vitamins, anti-cancer drugs, lung surfactant, omega-3 fatty acids, ethyl oleate, monolinoleic acid, caffeine, ephedrine, ketoprofen, metronidazole, acetyl salicylic acid, clotrimazole, vitamin E, insulin, lidocaine, hydrochloride, nitroglycerin, prilocaine, tetracycline hydrochloride, Benzylpenicillin, acyclovir, guaifenesin, melatonin, metronidazole, phenylpropanolamine, pseudophedrine hydrochloride, timolol maleate, acyclovir, hydrocortisone, minoxidil, sildenafil citrate, eflornithine HCl, zinc pyrithione, niacinamide, flavor oils, antibiotics, vitamins, fatty acids, tracer materials for diagnostic tests, pesticides, organophosphates, non-organophosphates, herbicides, and combinations thereof.

Even more preferably, the active ingredient can be selected from diazinon, diclofop-methyl, terrazole, vinclozolin, atrazine, oxamyl, propargite, triallate, and combinations thereof. Most preferably, the active ingredient can be selected from atrazine, nicosulfuron, carfentrazone, imazapyr, benefin, acifluorfen, and combinations thereof. It is also believed that the active ingredient can also be utilized as a hydrotrope and an active ingredient resulting in a combination of components D and E.

EXAMPLES

These examples are intended to illustrate the invention to those skilled in the art and should not be interpreted as limiting the scope of the invention set forth in the claims.

Example 1

Starch-Encapsulated Monoolein Powder

Powders were produced using a Yamato Pulvis Basic Spray Dryer Unit (FIG. 1). A twin-fluid nozzle with a liquid orifice size of 0.040 inches (0.1 cm) and an air orifice opening of 0.1 inches (0.25 cm) was inserted into the top of a Yamato Pulvis spray dryer body. The body of the spray dryer consisted of a drying chamber with a cyclone collector at the air exit. The spray dryer was set up for the heated, drying air to flow downward past the nozzle. The heated, drying air was set to a temperature of 200° C. Sonication of the liquid crystalline material was carried out using a Sonicator Ultrasonic Processor. A stir bar was used to keep the feed material agitated in the feed beaker at 25° C.

Spray-drying mixtures of monoolein (10% w/w), water (60%), and HI-CAP starch (30%) produced the first dry powder precursors. Assuming total removal of the added water, the resultant powder consisted of 25% monoolein and 75% starch. Subsequent measurements indicated that 4–10% moisture remained in the powders after drying. Upon hydration of the monoolein with the starch-water mixture, cubic liquid crystalline gel formed. As a result, homogeneous pumping of the material was not possible and high shear dispersion was used to create a suspension that could be spray dried. The dispersion was pumped through the liquid side of the twin-fluid atomizer at a rate of 15 mL/minute, with slight adjustments being made to keep the temperature of the exit air in the system at 90–95° C. The liquid feed was atomized with air at a pressure of 43 psi (296 kPa). The feed mixture was pumped until 20% of the material remained in the feed beaker.

Figure 2:
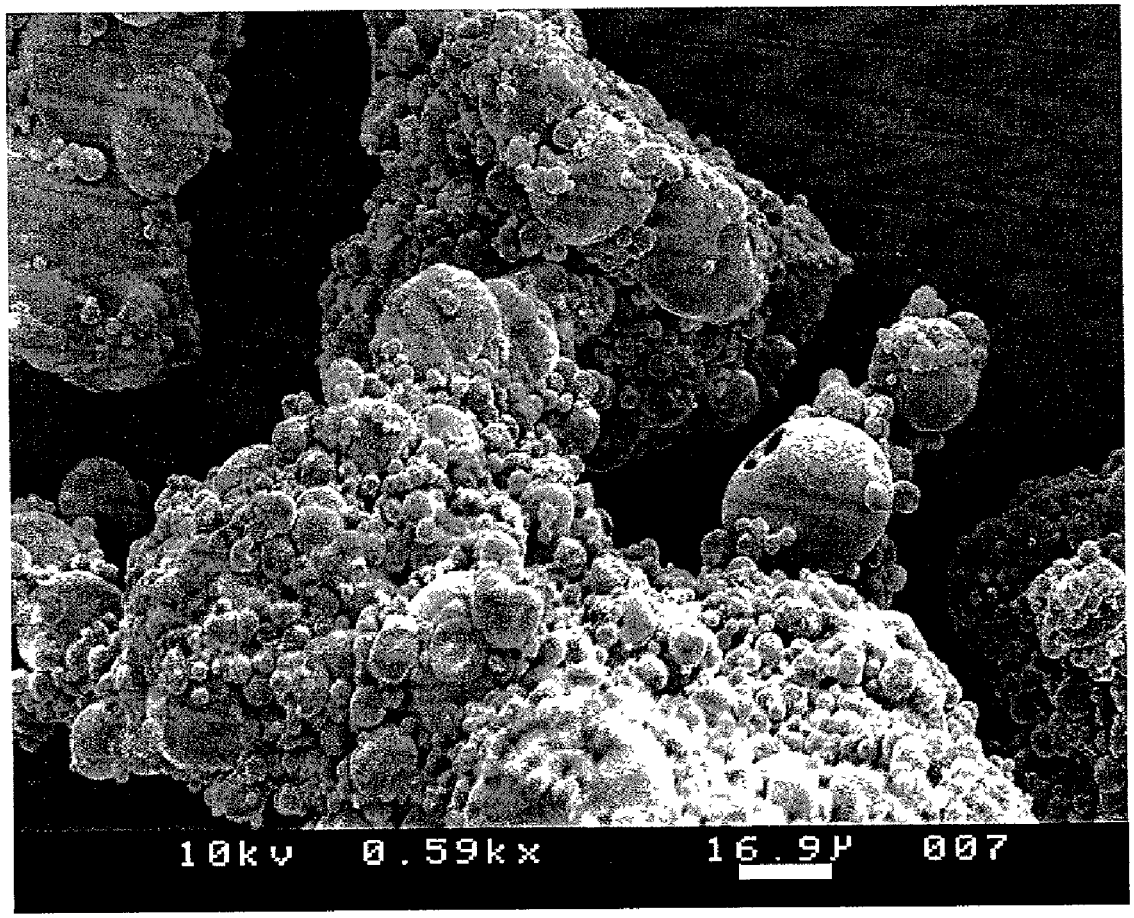
FIG. 2 is an SEM image of a cubic gel precursor prepared according to Example 1 of this invention.

The powders produced above were free flowing and fine. An exemplary SEM photograph of the powders formed by the above process is shown in FIG. 2. Numerous small and larger starch-encapsulated monoglyceride particles are shown in FIG. 2. Clearly, the particles are already well distributed into small units that will be easy to disperse and stabilize in water.

Figure 3:
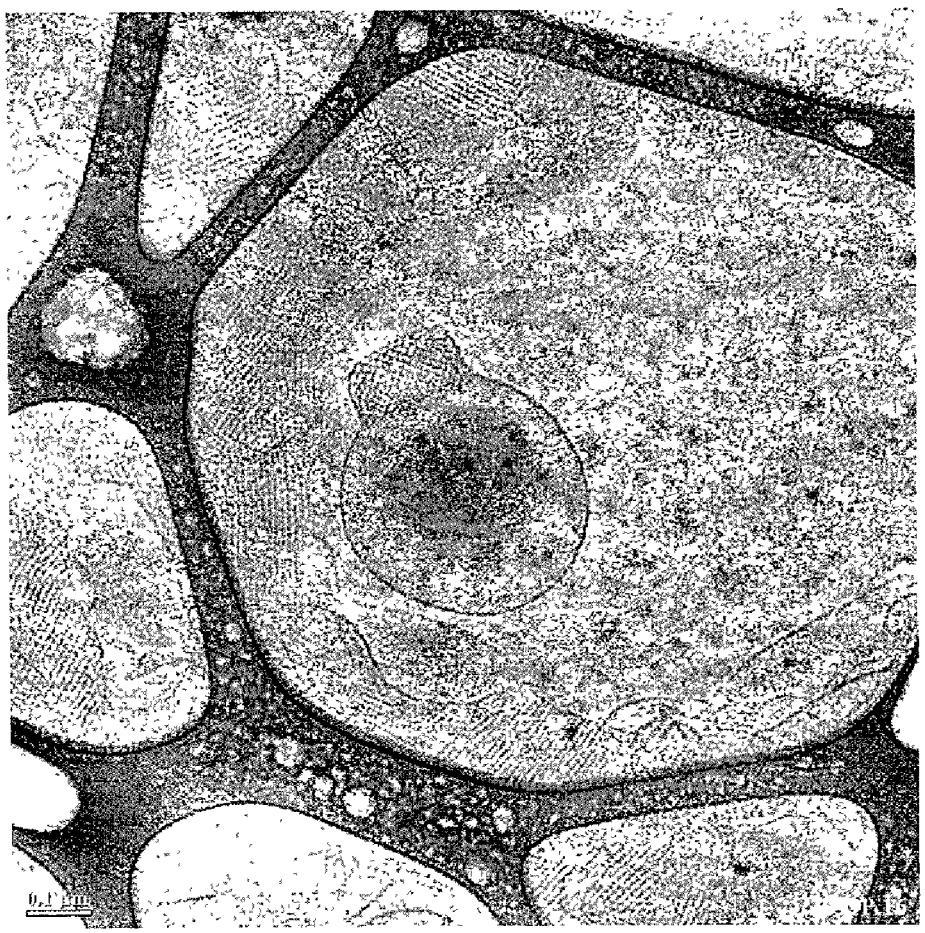
FIG. 3 is a cryo-TEM image of cubic gel particles prepared according to Example 1 of this invention.
Figure 4:
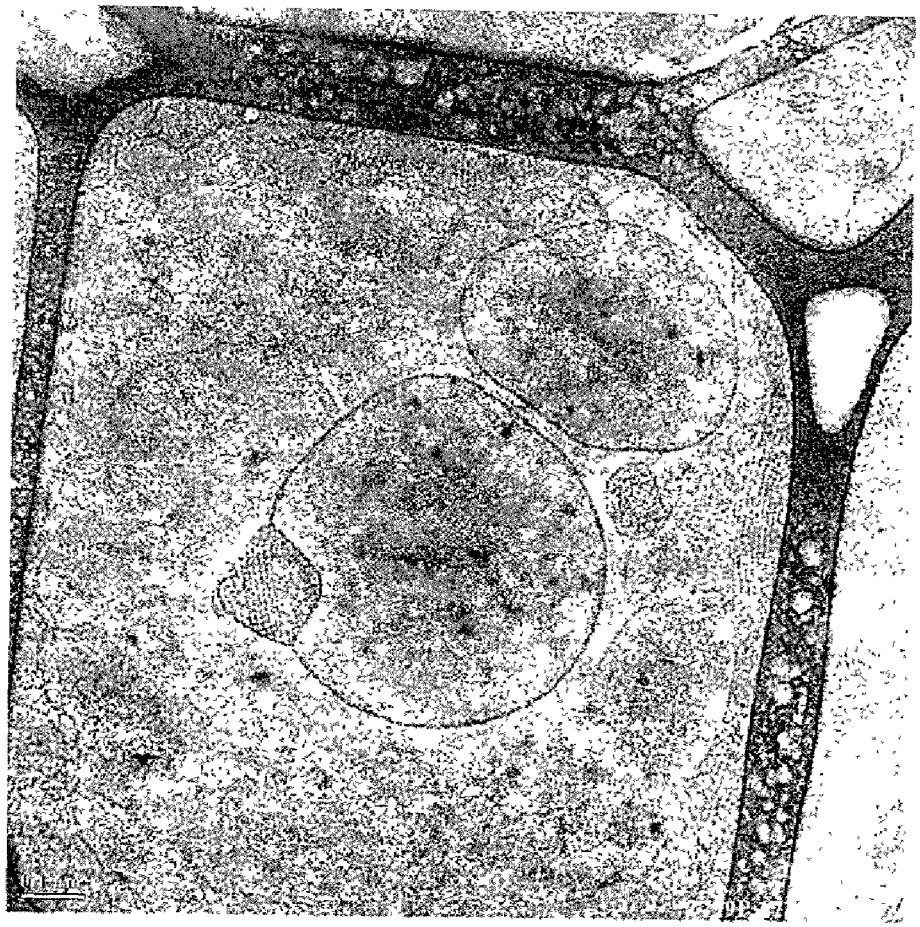
FIG. 4 is a cryo-TEM image of cubic gel particles prepared according to Example 1 of this invention.

Following the addition of the above powders to water, a remarkably fine dispersion was formed almost immediately with gentle stirring. No large agglomerates were evident from visual inspection, and optical microscopic observations of the dispersion revealed a uniform dispersion of sub-micron particles with regular shapes. A more detailed analysis of the particles formed by starch-monoolein powder hydration is shown using Cryo-TEM in FIGS. 3 and 4. In FIG. 3, a unique particle is visible that appears to be a hybrid complex of dispersed cubic liquid crystalline material (i.e. a cubosome) and a dispersed lamellar liquid crystalline particle or vesicle that is several times larger than the cubosome. Lamellar vesicles have been observed in cubosomes previously, and have been proposed as a thermodynamic means of avoiding exposure of lipid hydrocarbon chains as the cubic liquid crystalline gel is fragmented during dispersion. However, prior surface vesicles have been much smaller than the parent cubosome. Indeed, the complex in FIG. 3 is representative of the particles formed by starch-monoolein powder hydration, as FIG. 4 reinforces. In FIG. 4, a complex similar to that in FIG. 3 is seen, with similar cubosome and vesicle proportions.

Example 2

Starch-Monoolein-Hydrotrope Powders

It was found that the addition of sufficient amounts of a hydrotrope to aqueous monoolein systems produced low viscosity precursors that could be easily processed. Adaptation of those techniques here provides a means of more easily producing spray-dried cubosome precursors. The use of hydrotropes mimics the expected behavior for systems with active materials loaded, as many desirable actives are also hydrotropes. Instead of ethanol, sodium p-toluene sulfonate (STS) was chosen because of its high melting point. Powders were produced as in the case of starch-monoolein-water, with the mixture of monoolein (8% w/w), STS (8%), starch (24%), and water (60%) forming a flowable liquid that was easily pumped and kept homogeneous via stirring. The mixture was pumped at a rate of 6 mL/minute through the liquid side of the twin-fluid atomizer, with slight adjustments being made to the rate to keep the temperature of the exit air in the system to 90–95° C. The liquid feed was atomized with air at a pressure of 43 psi (296 kPa). The feed mixture was fed fully to the dryer.

Figure 5:
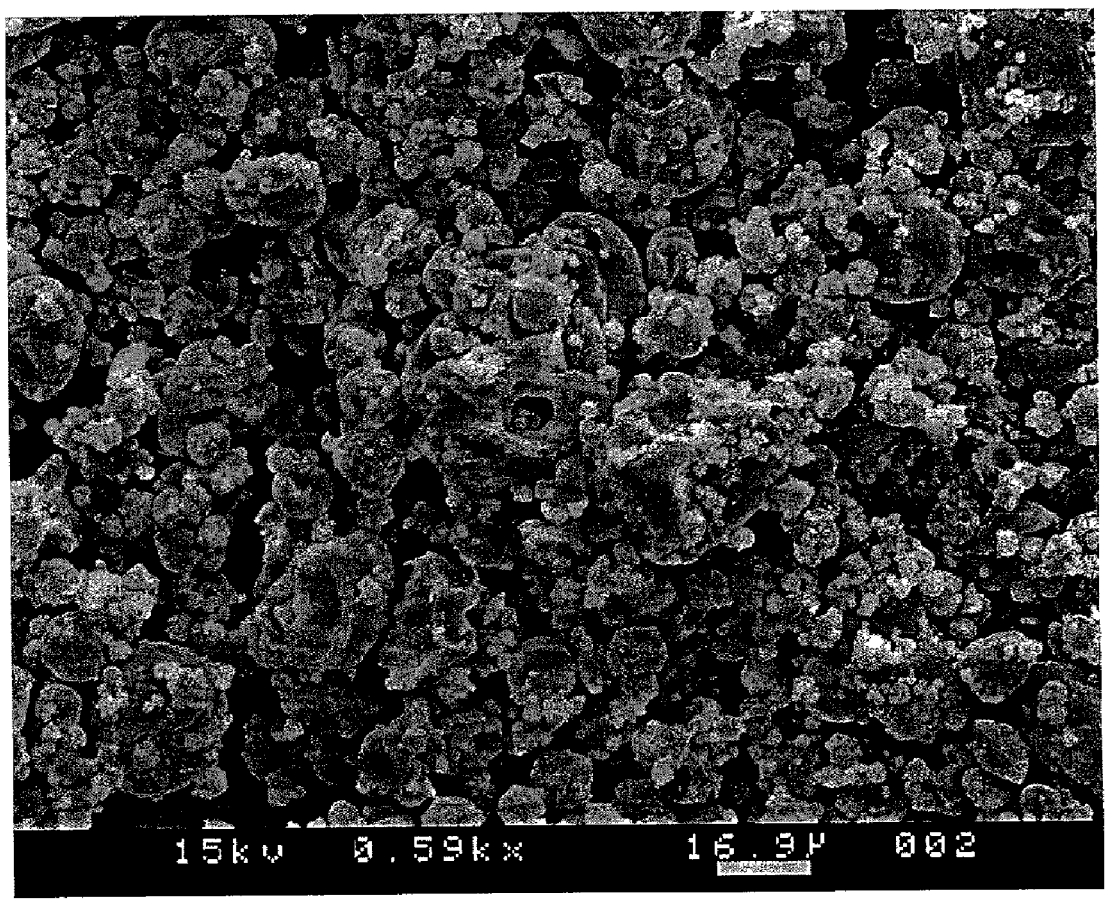
FIG. 5 is an SEM image of a cubic gel precursor prepared according to Example 2 of this invention.

FIG. 5 shows an SEM view of some starch/STS-encapsulated monoolein powder produced by the above process. Assuming complete drying occured, the final powder composition is 60% starch, 20% STS, and 20% monoolein. Hydration of the powders with water was used to move the system into the cubic liquid crystalline and water region of the phase diagram and form cubosomes. The particles in FIG. 5 resemble those in FIG. 2 in that they are irregular agglomerates of two sizes of primary particles: large and small, relatively hollow starch/STS capsules. Optical microscopy indicated that the powders produced with and without STS hydrotrope were remarkably similar, with no apparent effects of the STS on the bulk powder appearance. When the monoolein-STS-starch powders in FIG. 5 are hydrated, they dissolve and disperse rapidly into cubic particles, just as the starch-monoolein powders do.

Example 3

Encapsulation of Active Ingredients (Fatty Acid Solution) in Powders

The powder was made by spray-drying a liquid solution. The liquid solution was prepared from a premix of 67% water and 33% starch prepared at a temperature of 70° C. A second solution of 90% monoolein and 10% fatty acid mix (20% Omega-3, 80% triglyceride oil) was prepared at 60° C. The oil solution was then added to the starch-water solution forming a 9% monoolein, 30% starch, 60% water, and 1% fatty acid mixture. A high shear mixing system was used to keep the system mixed and maintained above 90° C. The mixture was then pumped at a rate of 8 mL/minute through the liquid side of a twin-fluid atomizer, with slight adjustments being made to the flow rate to keep the temperature of the exit air in the system between 90–100° C. The liquid feed was atomized with air at a pressure of 42.6 psi (293.5 kPa). Upon drying, the powder has a composition of 22.5% monoolein, 75% starch, and 2.5% fatty acid mixture.

The powders produced above are shown in FIG. 1 as photographed by SEM. The powder appears to exhibit a bimodal size distribution of larger 10 μm particles and smaller 3–5 μm particles, all of which exhibit the classical shrinkage that is characteristic of starch capsules during their cooling. The uniform appearance of the powders can be an excellent indicator that the fatty acid active is encapsulated within the starch shells.

Example 4

Encapsulation of Monoolein/Ethanol in Powders

The powder was formed by spray-drying a liquid emulsion. The liquid emulsion was prepared from a premix of 75 grams of water, 50 grams of dextran (average MW~37,500), 45-grams of ethyl alcohol, and a 30-gram measure of molten monoolein. The mixture had a final ratio of 37.5% water, 25% dextran, 22.5% ethyl alcohol and 15% monoolein. Observation indicated that this mixture was an emulsion of isotropic liquid in a lamellar and/or nematic liquid crystalline continuous phase. The mixture was then pumped at a rate of 3.92 grams per minute through the liquid side of a twin-fluid atomizer, with slight adjustments being made to the flow rate to keep the temperature of the exit air in the system between 125–135° C. The liquid feed was atomized with air at a pressure of 42.6 psi (293.5 kPa). The powders produced were comprised of 5–100 μm agglomerates of 1–10 μm primary particles that are likely dextran shells coating monoolein and residual ethanol (~10 w/w). Hydration of the powders produced mostly sub-micron cubic liquid crystalline particles in the range of at least about 0.1 m to at least about 10 m.

The foregoing examples and descriptions of the preferred embodiments of the invention have been presented for purposes of illustration and description only. They are not intended to be exhaustive or to limit the invention to the precise forms disclosed, and modifications and variations are possible and contemplated in light of the above teachings. While a number of preferred and alternate embodiments, systems, configurations, methods, and potential applications have been described, it should be understood that many variations and alternatives could be utilized without departing from the scope of the invention.

What is claimed is:

1. A cubic gel precursor comprising: (A) an encapsulating compound, (B) an amphiphile capable of forming a cubic liquid crystalline phase, and optionally (C) a solvent, wherein ingredients (A), (B), and optionally (C) are present in mass fractions relative to each other such that $1.0 = a + b + c$ wherein a is the mass fraction of ingredient (A), b is the mass fraction of ingredient (B), and c is the mass fraction of ingredient (C), and wherein the mass-fractional relationship between a, b and c is $0.75 \geq a \geq 0.5$, $0.5 \geq b \geq 0.25$, and $0.2 \geq c \geq 0$; and with the proviso that a, b, and c do not fall within a cubic liquid crystalline phase region on a phase diagram representing phase behavior of ingredients (A), (B), and (C).

2. The precursor of claim 1, wherein said encapsulating compound is selected from the group consisting of starch, cyclodextrin, dextran, and combinations thereof.

3. The precursor of claim 1, wherein said encapsulating compound further comprises (D) a hydrotrope.

4. The precursor of claim 1, wherein said encapsulating compound is selected from the group consisting of starch, cyclodextrin, dextran, and combinations thereof; and said encapsulating compound further comprises (D) a hydrotrope, wherein said hydrotrope is an active compound.

5. The precursor of claim 3, wherein said hydrotrope is selected from the group consisting of low molecular weight alcohols; polyols; alcohol ethoxylates; surfactants derived from mono- and poly-saccharides; copolymers of ethylene oxide and propylene oxide; fatty acid ethoxylates; sorbitan derivatives; sodium butyrate; poloxamer 407; polyethylene glycol 400; dimethyl sulfoxide; sodium toluene sulfonate; nicotinamide; procaine hydrogen chloride and the ethoxylated derivatives thereof; ethylene glycol, sodium alkanoates, sodium alkane sulfonates, resorcinol, pyrogallol, PABA hydrogen chloride, sodium p-bromobenzene sulfonate, isonicotinic acid, sodium 4-picolinate, sodium 3-hydroxy-2-napthlate, sodium xylene sulfonate, sodium cinnamate, sodium benzene disulfonate, sodium p-toluenesulfonate, sodium salicylate, sodium benzene sulfonate, sodium benzoate, sodium cumeme sulfonate, propylene glycol, glycerol, and polyglyceryl esters, caffeine, sodium butyrate; and combinations thereof.

6. The precursor of claim 1, wherein said precursor further comprises a hydrotrope which is selected from the group consisting of low molecular weight alcohols; polyols; alcohol ethoxylates; surfactants derived from mono- and poly-saccharides; copolymers of ethylene oxide and propylene oxide: fatty acid ethoxylates: sorbitan derivatives; sodium butyrate; poloxamer 407; polyethylene glycol 400; dimethyl sulfoxide; sodium toluene sulfonate; nicotinamide: procaine hydrogen chloride and the ethoxylated derivatives thereof; ethylene glycol, sodium alkanoates, sodium alkane sulfonates, resorcinol, pyrogallol, PABA hydrogen chloride, sodium p-bromobenzene sulfonate, isonicotinic acid, sodium 4-picolinate, sodium 3-hydroxy-2-napthlate, sodium xylene sulfonate, sodium cinnamate, sodium benzene disulfonate, sodium p-toluenesulfonate, sodium salicylate, sodium benzene sulfonate, sodium benzoate, sodium cumeme sulfonate, propylene glycol, glycerol, and polyglyceryl esters, caffeine, sodium butyrate; and combinations thereof.

7. The precursor of claim 1, wherein said amphiphile is selected from the group consisting of glycerol monooleate, glycerol monostearate, monolinolein, ethyoxylated alcohol surfactants, and combinations thereof, wherein said solvent is selected from the group consisting of water, glycerol, glycols, formamides, ethylammonium nitrate, and combinations thereof; and said glycol is selected from the group consisting of ethylene glycol, polyethylene glycol, and combinations thereof.

8. The precursor of claim 1, further comprising: (E) an active ingredient.

9. The precursor of claim 8 wherein said active ingredient is selected from the group consisting of proteins, amino acids, vitamins, anti-cancer drugs, lung surfactant, omega-3 fatty acids, ethyl oleate, monolinoleic acid, caffeine, ephedrine, ketoprofen, metronidazole, acetyl salicylic acid, clotrimazole, vitamin E, insulin, lidocaine, hydrochloride, nitroglycerin, prilocaine, tetracycline hydrochloride, benzylpenicillin, acyclovir, guaifenesin, melatonin, metronidazole, phenyipropanolamine, pseudoephedrine hydrochloride, timolol maleate, acyclovir, hydrocortisone, minoxidil, sildenafil citrate, eflomithine HCl, zinc pyrithione, niacinamide, flavor oils, antibiotics, vitamins, fatty acids, tracer materials for diagnostic tests, pesticides, organophosphates, non- organophosphates, herbicides, and combinations thereof.

10. The precursor of claim 9 wherein said organophosphate is diazinon.

11. The precursor of claim 9 wherein said non-organophosphate is selected from the group consisting of diclofop methyl, terrazole, vinclozolin, atrazine, oxamyl, propargite, triallate, and combinations thereof.

12. The precursor of claim 9 wherein said herbicide is selected from the group consisting of atrazine, nicosulfuron, carfentrazone, imazapyr, benefin, acifluorfen, and combinations thereof.

13. A method of making the precursor of claim 1 comprising the steps of: (A) dissolving an encapsulating compound in a solvent: (B) adding an amphiphile; (C) mixing said encapsulating compound and said amphiphile, wherein steps (A), (B), and (C) are performed in any order; (D) atomizing said mixture; and, (E) drying said mixture; and (F) adding a hydrotrope prior to step (D) and wherein step (E) is carried out by a process selected from the group consisting of freeze drying, spray drying, fluidization, complex coacervate formation, co-extrusion and combinations thereof.

14. The method of making the precursor of claim 13 comprising the additional step of: (G) adding an active ingredient prior to step (D).

15. The precursor of claim 1, wherein said amphiphile is selected from the group consisting of 3,7,11,15-tetramethyl-1,2,3-hexadecanetriol, (phytantriol), N-2-alkoxycarbonyl derivatives of N-methylglucamine, unsaturated fatty acid monoglycerides, and combinations thereof; and wherein said solvent is selected from the group consisting of water, glycerol, glycols, formamides, ethylammonium nitrate, and combinations thereof.

16. The precursor of claim 15, wherein said glycol is selected from the group consisting of ethylene glycol, polyethylene glycol, and combinations thereof.

* * * * *

UNITED STATES PATENT AND TRADEMARK OFFICE
CERTIFICATE OF CORRECTION

PATENT NO. : 7,008,646 B2  Page 1 of 1
APPLICATION NO. : 09/990552
DATED : March 7, 2006
INVENTOR(S) : Lynch et al.

It is certified that error appears in the above-identified patent and that said Letters Patent is hereby corrected as shown below:

Claim 6; line 50; syllabication incorrect should read: and poly-glyceryl

Signed and Sealed this

Twenty-fifth Day of July, 2006

JON W. DUDAS
*Director of the United States Patent and Trademark Office*